United States Patent [19]

Lapeyre et al.

[11] Patent Number: 4,654,033
[45] Date of Patent: Mar. 31, 1987

[54] DEVICE FOR ATRAUMATIC ACCESS TO THE BLOOD CIRCUIT

[75] Inventors: Didier Lapeyre, Chaignes; Jean-Pierre Slonina, Le Vesinet, both of France

[73] Assignee: Biomasys, Precy-Sous-Thil, France

[21] Appl. No.: 718,379

[22] Filed: Apr. 1, 1985

[30] Foreign Application Priority Data

Apr. 2, 1984 [FR] France .................. 84 05141

[51] Int. Cl.⁴ .............................................. A61M 5/00
[52] U.S. Cl. .................................... 604/175; 604/891;
604/905; 604/236
[58] Field of Search .............. 604/175, 51, 52, 236,
604/237, 267, 905, 891

[56] References Cited

U.S. PATENT DOCUMENTS

| | | | |
|---|---|---|---|
| 3,783,868 | 1/1974 | Bokros | 604/891 |
| 4,015,601 | 4/1977 | Bokros et al. | 604/175 |
| 4,108,174 | 8/1978 | Slivenko | 604/175 |
| 4,164,221 | 8/1979 | Bentley et al. | 604/175 |
| 4,344,435 | 8/1982 | Aubin | 604/175 |
| 4,349,021 | 9/1982 | Raible | 604/175 |
| 4,350,157 | 9/1982 | Hoffa | 604/175 |
| 4,421,507 | 12/1983 | Bokros | 604/175 |
| 4,425,119 | 1/1984 | Berglund | 604/175 |
| 4,496,350 | 1/1985 | Cosentino | 604/175 |
| 4,512,761 | 4/1985 | Raible | 604/905 |
| 4,534,761 | 8/1985 | Raible | 604/175 |
| 4,597,756 | 7/1986 | Raible | 604/175 |

OTHER PUBLICATIONS

"An Introduction to Carbon Composite Materials", by J. W. Warren and C. D. Coulbert (1971).
"Characterization of Advanced Solid Rocket Nozzle Materials", by J. G. Baetz, (1976).
"CVD/PAN Felt Carbon/Carbon Composites", vol. 9, Oct. 1975.

Primary Examiner—Stephen C. Pellegrino
Assistant Examiner—John D. Ferros
Attorney, Agent, or Firm—Oblon, Fisher, Spivak, McClelland, & Maier

[57] ABSTRACT

A device for a traumatic access to a blood vessel of a living organism through the cutaneous surface thereof. The device includes in combination an implantable device comprising a tubular segment for access to the blood vessel; a valving element for the tubular segment; a mechanism for controlling the blood flow through the valving element; a cover for sealing the proximal end of the tubular segment in the absence of the blood control mechanism; and a porous coating adapted to be colonized by tissue ingrowth and at least partially surrounding the implantable device. The porous coating is formed from a carbon-carbon composite material comprising a reinforcement formed from a carbon fiber porous substrate embedded in a carbonaceous matrix design to densify only partially the fiber substrate while connecting the carbon fibers together.

17 Claims, 8 Drawing Figures

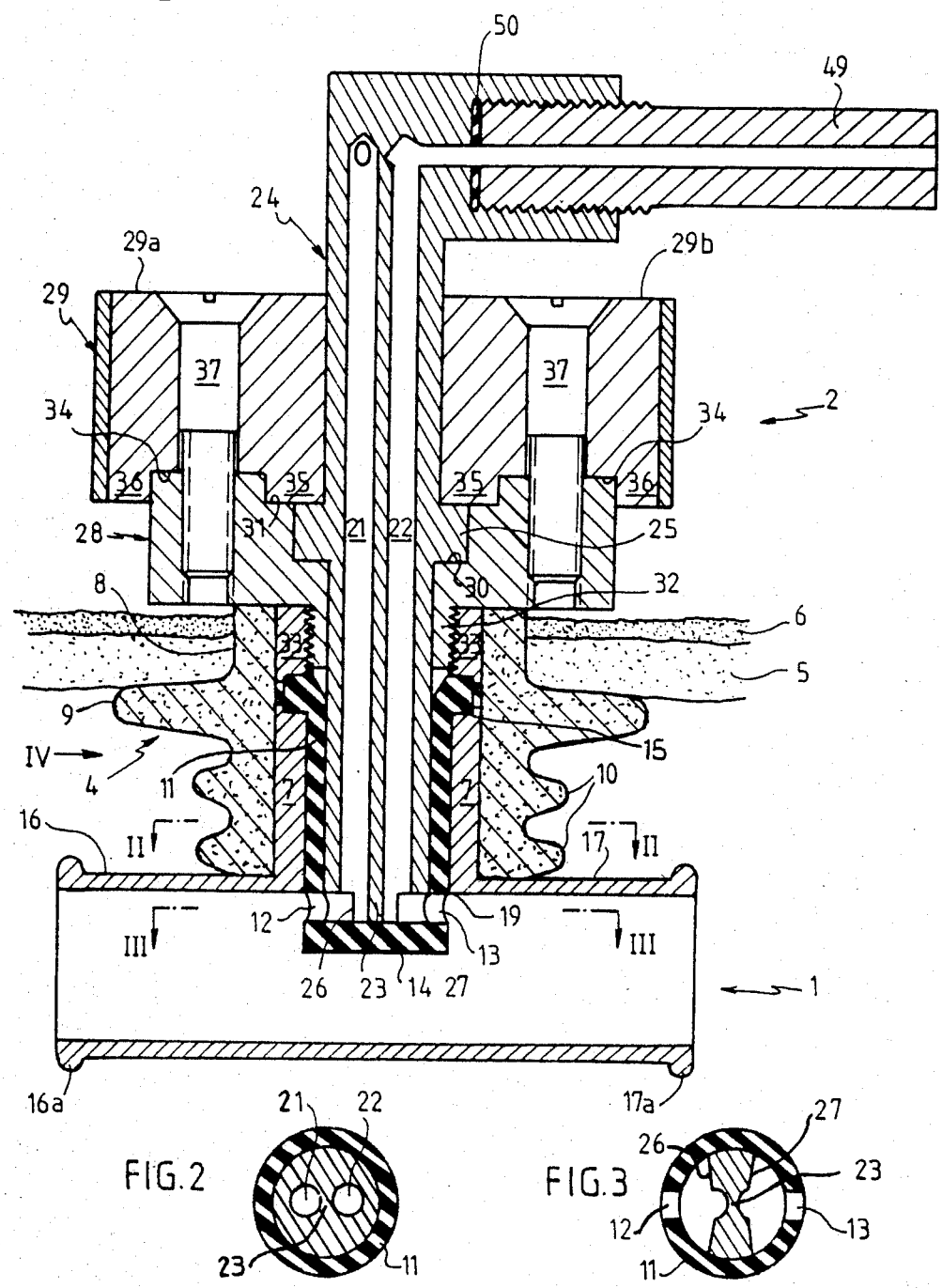

DEVICE FOR ATRAUMATIC ACCESS TO THE BLOOD CIRCUIT

BACKGROUND OF THE INVENTION

1. Field of the Invention

The present invention relates to a device for a traumatic or non traumatic access to the blood circuit. The device is of the type comprising an implantable device for taking blood percutaneously and a mechanism controlling the blood flow. More particularly, the invention relates to a device for providing extra-corporeal circulation of the blood in order to compensate for poor functioning of the kidneys.

2. Description of the Prior Art

A device is already known for giving access to the blood circuit comprising a T-shaped percutaneous device formed as a single piece from a biologically compatible material, such as titanium.

In this prior art device, the lateral segments of the T each have an annular retaining flange and may be inserted directly in a blood vessel that has been previously split longitudinally and then sutured. Alternatively, the lateral segments of the T may be inserted in the middle of an artificial blood duct made from expanded polytetrafluoroethylene and used to form a shunt between an artery and a vein of fairly large diameters.

The central segment of the T comprises a closure element providing sealing with respect to the lateral segments. The central segment is formed with a transverse circular dividing wall made from silicon elastomer. The transverse circular dividing wall has two slits formed along the same diameter, spaced from the edge of the wall, and separated by a solid central part. A needle or cannula device connected to the blood cleansing system may be introduced into each of the slits. The centering of the needle or cannula device with respect to each slits is obtained by two semispherical depressions centered about the slits.

The needle or cannula devices are held clamped by means of an elastomer toroidal clamping ring inserted in a circular groove formed in the thickness of the transverse circular dividing wall. The clamping ring provides the required functional sealing.

The transverse circular dividing wall is held in position by means of a transverse compression plate formed as a single piece with a tubular compression ring. The tubular compression ring is force fitted in the cavity of the central segment of the T and is held in position by means of two projections which project outwardly from the upper edge of the transverse compression plate. The two projections snap fit into a circular groove formed in the vicinity of the corresponding edge of the central segment of the T.

The transverse compression plate has two orifices corresponding to the two previously mentioned slits. The transverse compression plate separates an upper chamber from a lower chamber. In the lower chamber, the upper part of the transverse circular dividing wall is imprisoned by force. An eccentric alignment stud juts out between the slits and the orifices. The eccentric alignment stud projects from the lower surface of the transverse compression plate and is housed in a corresponding cavity in the transverse circular dividing wall.

The prior art percutaneous device may have a pyrolytic carbon coating for increasing its biocompatibility. It may further have, except on the upper part of the central segment of the T, a coating of a porous material such as polyethylene terephtalate or porous titanium. The porous material forms a supporting structure which may be colonized by tissue growth.

The tubular compression ring may be made from a biocompatible metal. Alternatively, the tubular compression ring may be made by injection molding of a plastic material such as polycarbonate or polysulfone, possibly reinforced with a glass, carbon, or mineral charge.

Insertion and extraction of the assembly consisting of the transverse circular dividing wall and the tubular compression ring is achieved by means of tools specially designed for this purpose.

A second prior art device is known for giving access to the blood circuit. The second prior art device may also be connected to a blood vessel directly or through an arterial-venous shunt.

The second prior art device comprises a percutaneous device formed by a conical blood flow duct made from a biocompatible material. The conical blood flow duct is non-porous- and non-biodegradable, and it may be made from pyrolytic carbon deposited on a graphite substrate or from vitreous carbon the external surface of which has a smooth appearance. The conical blood flow duct comprises at the distal end a first perforated fixing collar and, in the intermediate part, a second perforated fixing collar for biological anchorage through invasion of the perforations by tissue growth.

The second prior art also comprises a closure element, solid and also conical, for the conical blood flow duct. The closure element ends in a non-conical proximal part improving the sealing.

The percutaneous device cooperates with an atraumatic mechanism for controlling the blood flow through a rod actuated from the outside which is screwed into the closure element after passing through an orifice formed in a closure chamber of the conical flow duct. The closure chamber is in communication with a blood treatment device through a single tube. The blood is alternately drawn through the single tube for treatment, then returned to the body. Alternatively, the blood may be circulated by means of two tubes, the first of which is intended for drawing off the blood and the second of which is intended for returning the blood simultaneously to the body. The control mechanism also cooperates with a ring for fixing the closure chamber against a flange of the conical blood flow duct.

The conical blood flow duct comprises at least a partial coating disposed between the first and second perforated fixing collars. The coating is made from a vascular grafting material such as polyethylene terephtalate. Additionally, the coating comprises a partial microporous coating impermeable to blood, and thus minimizing the blood loss, which is applied in correspondence with the first perforated fixing collar and is made from polytetrafluoroethylene.

The conical closure element may also have two channels separated by a longitudinal central dividing wall connected to its base. The base closes the flow duct in the rest condition.

The two channels each communicate, at the lower part, with a transverse orifice formed in the vicinity of the base of the conical closure element. Additionally, the two channels each communicate, in the upper part, with a tubular flow chamber connected to a blood treatment device.

In this case, using an appropriate control tool, the conical closure element, connected to the tubular flow chambers, may be lowered and the base of the conical closure element with the transverse orifices plunged in the blood flow, thus establishing the desired extracorporeal circulation. By actuating the control tool in the opposite direction, the conical closure element with the tubular flow chambers may be raised, which causes closure of the transverse orifices and stops the extracorporeal circulation.

In the rest condition the base closes the flow duct, and the conical closure element has a certain functional play with respect to the walls of the flow duct. That play is just sufficient to allow it to be lowered into the open position, so that the transverse orifices are again exposed to the blood flow.

The prior art has drawbacks, more especially:
in so far as the percutaneous device is concerned:
  the reliability and cleaning are problematical;
  the porous coating which may be colonized by tissue growth has, because of the materials used up to present and with respect to the organic tissues, biological affinity which is far from being total, which also prevents in this case a truly intimate anchorage, so
  the resistance to accidental tearing forces exerted at the junction of the skin is low, which creates "marsupialization" of the skin with risks of infection;
in so far as the blood flow control mechanism is concerned, it comprises numerous parts, which are often difficult to clean, resulting in a greater risk of clotting or insufficient asepsis; and
in so far as the access device to the blood circuit as a whole is concerned, it requires the use of numerous accessory tools, which complicates the use of the access device.

OBJECTS OF THE INVENTION

The aim of the present invention is consequently to provide a device for a traumatic or non-traumatic access to the blood circuit of the type comprising an implantable percutaneous device and a mechanism for controlling the blood flow which answers better the requirements of practice than the previously known devices used for the same purposes. In particular, it is the aim of the present invention to provide such a device which is an improvement over the prior art in one or more of the following respects:
the biological anchorage of the percutaneous device by tissue growth is more intimate, which ensures
  a higher resistance to accidental tearing forces exerted at the junction of the skin, and
  a more efficient barrier against the penetration of bacteria at the seat of the implantation, thus eliminating risks of infection;
sealing and cleaning of the percutaneous device are more reliable;
actuation of the control mechanism does not require any tools, which makes it particularly simple and reliable; and
the parts of the control mechanism are reduced to a minimum and their shape is such that cleaning is very easy and reliable, which eliminates the risk of stopping the blood flow by clotting or insufficient asepsis.

SUMMARY OF THE INVENTION

The present invention provides a device for atraumatic access to the blood circuit of the type comprising in combination:
  an implantable device having a tubular segment for access to a blood vessel and projecting slightly from the cutaneous surface;
  a control device for controlling the blood flow through the closure element, the control device having a proximal part and a distal part; and
  a cover for closing the tubular segment giving access to the blood.

The closure element is formed by a tubular piece made from a hemocompatible resilient material inserted inside the tubular segment giving access to the blood. The closure element is closed at its base and is provided with at least one lateral orifice which, in use, communicates with a blood vessel. The closure element additionally comprises means for retaining it in position in a blood vessel. The at least one lateral orifice of the closure element is closed by the wall of the tubular segment in the absence of the control device. The closure element is extended resiliently, when the control device is present, by the axial thrust of the distal part of the central device on the base of the closure element, thereby immersing the base and the at least one lateral orifice in the blood stream. The closure element resumes its original dimensions under the action of the stress due to its resilient extension when the control device is withdrawn.

In a preferred embodiment of the device giving access to the blood circuit in accordance with the invention, the means for retaining the closure element in position in a blood vessel preferably comprise an annular collar formed about the opening giving access to the closure element. The annular collar is provided with a plurality of transverse anti-rotation studs formed in the thickness of the collar. The tubular segment of the implantable device has a circular groove sized, shaped, and positioned to house the annular collar. The transverse anti-rotation studs are housed in their turn in orifices pierced in the wall of the tubular segment which corresponds to the circular groove. The circular groove is formed in the internal wall of the tubular segment at a distance from the access orifice to the tubular segment such that, in the absence of application of the control device or the cover, the base of the closure element is slightly set back with respect to the base of the tubular segment.

In an advantageous embodiment of the access device to the blood circuit in accordance with the invention, the at least one lateral orifice communicating with the blood vessel is formed substantially at the intersection of the base sealing the closure element with the lateral wall of the closure element.

In an advantageous arrangement of this embodiment, the at least one lateral orifice is oblong and is formed with the blood flow axis of the at least one orifice slanting with respect to the blood vessel at an acute angle (which is preferably 60°) with respect to the axis of the closure element. The at least one lateral orifice passes substantially through the intersection point between the base and the lateral wall.

According to another advantageous embodiment of the access device to the blood circuit in accordance with the invention, the base sealing the closure element has outwardly an arcuate configuration for reducing the turbulence due to the immersion of the base in the blood stream. The arcuate configuration is defined cross wise (that is, perpendicularly to the blood flow direction) by two substantially triangular lateral projections which are aligned with the lateral wall of the closure element.

According to another advantageous embodiment of the access device to the blood circuit of the invention, when this device is of the type comprising a blood flow control mechanism having two tubular flow chambers communicating with two end pieces connected to a blood cleansing device which are provided with diametrically opposite notches, more especially in the form of a V with a wide opening, and which are joined together by a longitudinal central dividing wall and an outer sheath common to the two tubular flow chambers, the sheath of the two tubular flow chambers comprises an annular collar. The annular collar is formed substantially in the middle part of the outer sheath. The two tubular flow chambers extend bilaterally with respect to the annular collar in the distal and proximal parts. The annular collar is intended to cooperate with means locking the two tubular flow chambers and driving the distal part of the central device by roto-translation inside the closure element.

According to an advantageous arrangement of this embodiment, the locking and drive means of the two tubular flow chambers are formed by a knurled nut having a cylindrical body. The cylindrical body of the knurled nut comprises a first central seat housing the annular collar projecting from the sheath of the two tubular flow chambers. A second central centering seat is superimposed on the first one. The second central centering seat is of a larger diameter than the first one. A central projecting part of the cylindrical body is disposed on the side opposite the first and second central centering seats. The central projecting part is in communication with the first and second central centering seats and threaded on its outer surface for screwing into a tapped portion of the tubular segment of the implantable device situated above the circular groove. A coaxial fixing ring is superimposed with respect to the knurled nut. The coaxial fixing ring is formed from two half rings each comprising, on a transverse face, a semicircular groove defining centrally a part sized, shaped, and positioned to be housed and centered in the second central centering seat of the coaxial fixing ring and to imprison, with the knurled nut, the annular collar of the two tubular flow chambers in the first coaxial centering seat. Laterally each semicircular groove defines a part sized, shaped, and positioned to partially envelope the knurled nut. The two half rings and the knurled nut are preferably secured together by means of screws.

According to another advantageous embodiment of the access device to the blood circuit of the invention, the annular collar comprises a closure plate sized, shaped, and positioned to cover the tubular segment of the implantable device as well as its coating. A first central cylindrical part projects from the closure plate and is threaded for screwing into the tapped portion of the tubular segment.

In a preferred embodiment of the access device to the blood circuit in accordance with the invention, the cover comprises a second central projecting cylindrical part, smaller in diameter than the first threaded projecting part. The second central projecting part juts out from the first threaded projecting part inside the tubular closure element and is surrounded by a pressure sleeve extending as far as the base of the tubular closure element. The second central projecting part is force fit in the first threaded projecting part. The pressure sleeve is therefore secured against rotation and compresses the lateral wall of the closure element against the wall of the tubular segment of the implantable device, while allowing free rotation of the second part projecting inside the pressure sleeve.

In another preferred embodiment of the access device to the blood circuit in accordance with the invention, the cover has a third central cylindrical part which projects from the second projecting part and which has a smaller diameter than the second projecting part. The third projecting part is surrounded by a retaining washer. The retaining washer has a diameter smaller than that of the second projecting part. The retaining washer is held against the second projecting part by a splaying out or widening out of the distal end of the third projecting part The widening out of the distal end of the third projecting part is formed by crimping or hot forming the distal end. The cylindrical groove defines a shoulder against which the retaining washer is applied. The shoulder holds the pressure sleeve in position.

According to another advantageous embodiment of the access device to the blood circuit in accordance with the invention, the closure plate of the cover comprises an annular seal force fitted into a circular groove formed in the closure face of the plate.

According to another preferred embodiment of the access device to the blood circuit in accordance with the invention, when it is of the type comprising in addition a coating of a porous material which may be colonized by tissue growth and which surrounds at least partially the implantable device, the porous coating is formed by a composite carbon-carbon material of the type comprising a reinforcement formed by a porous carbon fiber substrate embedded in a carbonaceous matrix for densifying the porous carbon fiber substrate and connecting the carbon fibers together. In the composite carbon-carbon material, the porous carbon fiber substrate is densified only partially by the carbonaceous matrix so as to obtain a porous carbon-carbon composite material.

According to an advantageous arrangement of this embodiment, the porosity of the composite material is preferably between 40% and 50% of the original porosity of the carbon fiber substrate.

According to another advantageous embodiment of the access device to the blood circuit in accordance with the invention, the porous coating completely surrounds at least the tubular segment of the implantable device over the whole of its length, including the part thereof which projects slightly from the epiderm. The porous coating comprises a substantially cylindrical proximal part the height of which is slightly greater than the total thickness of the derm and of the epiderm. The porous coating is followed by a circular collar-shaped intermediate part providing the main biological anchorage.

According to a preferred arrangement of this embodiment, the substantially cylindrical proximal part of the porous carbon-carbon composite coating comprises a solid pyrolytic carbon film. The solid pyrolytic carbon film is sealing and non-porous. The solid pyrolytic carbon film protects against the penetration of harmful agents such as dust, liquids, or the like. The solid pyrolytic carbon film is applied to the exposed portion of the coating parallel to the epiderm as well as to a small portion of the external lateral surface of the tubular segment perpendicular to the epiderm.

In addition to the preceding arrangements, the invention further comprises other arrangements which will be clear from the following description.

BRIEF DESCRIPTION OF THE DRAWINGS

The invention will be better understood from the remainder of the description which follows with reference to the accompanying drawings in which:

FIG. 1 shows a sectional view of the device for atraumatic access to the blood circuit.

FIGS. 2 and 3 are sectional views, along the lines II—II and III—III, respectively, of the device shown in FIG. 1.

FIG. 6 is an elevation view in the direction of the blood flow;

FIG. 7 is a sectional view along the line VII—VII in FIG. 6; and

FIG. 8 is a top view.

It should of course be understood that these drawings and corresponding descriptive parts are given solely by way of illustration of the subject of the invention and that they form in no wise a limitation.

DESCRIPTION OF THE PREFERRED EMBODIMENTS

Figure 4:
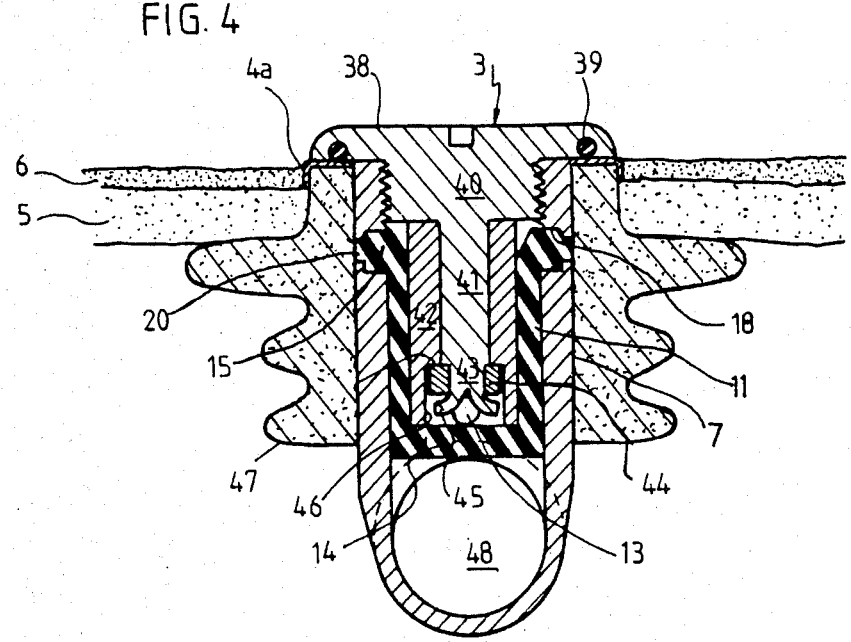
FIG. 4 shows a sectional view of the percutaneous device taken in the direction of the arrow IV in FIG. 1.

The device for a traumatic access to the blood circuit of the invention is of the type comprising an implantable percutaneous device 1 which is preferably in the form of a T and which cooperates during renal dialysis with a blood flow control mechanism 2 and, under normal conditions, with a cover 3 (shown in FIG. 4). The percutaneous device 1 is formed as a single piece having two lateral segments 16 and 17 and a central segment 7 having a base 19. The percutaneous device 1 is preferably made from titanium. However, the use of stainless steel may also be considered.

A porous coating 4 surrounds the percutaneous device 1. The porous coating 4 is composed of carbon-carbon composite materials, which are well known to technicians in the art.

A carbon-carbon composite is formed from two elements:
  a porous carbon fiber substrate serving as reinforcement and
  a carbonaceous matrix for densifying the porous carbon fiber substrate and for providing connection between the carbon fibers.

Densification of the porous carbon fiber substrate is obtained by two main techniques:

(1) by chemical deposition in the vapor phase of pyrolytic carbon about the carbon fibers in the porous carbon fiber substrate. The pyrolytic carbon is obtained by thermal decomposition of a gaseous hydrocarbon under defined conditions of temperature and pressure (about 1000° C. and about 10 torrs). The crystallites of the pyrolytic carbon matrix thus obtained are oriented substantially parallel to the axis of the carbon fibers.

(2) by impregnation of the porous carbon fiber substrate with an organic liquid which is then carbonized so as to leave only a coke skeleton.

In so far as the present invention is concerned, it is the first of the two techniques which have just been outlined which is really interesting, since it allows the densification of the porous carbon fiber substrates and so the final porosity of the carbon-carbon composite to be controlled. Control of the density of the carbon-carbon composite is used to adapt the carbon-carbon composite to the colonisation of the fibroblasts generated by the underside of the derm 5. Preferably the porosity of the porous coating 4 is between 40% and 50% of the initial porosity of the porous carbon fiber substrate. The carbon fibers are preferably substantially perpendicular to the derm 5 and to the epiderm 6.

The final density of the porous carbon-carbon composite material is preferably between 0.8 and 1.2 g/cm$^3$.

The pores of the porous carbon have a diameter between 12 and 15 micrometers, which ensures, with respect to the other porous coatings proposed in the prior art (such as porous titanium or polyethylene terephtalate) a more intimate colonisation on the part of the fibroblasts, giving rise to the formation of collagen with a more efficient biological anchorage.

The porous coating 4 completely surrounds the central segment 7 of the percutaneus device 1 over the whole of its length, including the part of the percutaneous device 1 which projects slightly from the epiderm 6.

The porous coating 4 comprises:
  a substantially cylindrical proximal part 8. The height of the proximal part 8 is slightly greater than the total thickness of the derm 5 and the epiderm 6.
  an intermediate part in the form of a circular collar 9. The collar 9 ensures the main biological anchorage of the porous coating 4 and is disposed just under the derm 5.
  a distal part comprising a plurality of circular ribs 10. The circular ribs 10 provide an additional biological anchorage.

The proximal part 8 of the porous coating 4 may be advantageously coated, at the exposed portion parallel to the epiderm 6 and at the external lateral portion perpendicular to the epiderm 6, with a thin film 4a (cf. FIG. 4). The thickness of the thin film 4a is preferably of the order of a few hundredths of a millimeter. The thin fiber 4a is made from solid pyrolytic carbon, which is sealing and non porous. The thin film 4a protects the porous coating 4 from any harmful impregnation—in particular by dust, liquids, or the like.

The percutaneous device 1 also comprises a closure element 11 which, according to the invention, is a tubular piece made from a hemo-compatible resilient material such as polyurethane. The closure element 11 is preferably obtained by molding and has a sealing base 14.

Two diametrically opposite orifices 12 and 13, intended for withdrawing and reinjecting the blood respectively, are formed in the distal end of the closure element 11, substantially at the level of the intersection of the sealing base 14 of the closure element 11 with the lateral wall thereof. An annular retaining collar 15 is located at the proximal end of the closure element 11. In the absence of the blood flow control mechanism 2, the orifices 12 and 13 do not open into the blood stream defined by the lateral segments 16 and 17 of the percutaneous device 1.

Two annular ridges 16a and 17a promote the joining together of the percutaneous device 1 and the arterial-venous shunt in which it is preferably disposed during use. The ridges 16a and 17a prevent the shunt from sliding.

Sealing is provided (cf. FIG. 4) by the sealing base 14 of the closure element 11. Additionally, the closure element 11 is force fitted into the central segment 7.

The annular retaining collar 15 is housed in a circular groove 18 which is formed in the internal wall of the central segment 7 of the percutaneous device 1 at a distance from the access orifice to the central segment 7 such that, in the absence of application of the blood flow control mechanism 2 or the cover 3 (namely, in the rest condition), the sealing base 14 of the closure element 11 is located appreciably above the base 19 of the central segment 7 (for example, from 0.6 to 1 mm). Accordingly, with aging (namely, the variation in time of the resilient properties of the material from which the closure element 11 is formed), the closure element 11 does not project beyond the base 19, which would be an undesirable source of clot formation.

Transverse studs 20 are molded integrally as parts of the closure element 11. The transverse studs 20 secure the annular retaining collar 15 against rotation and are engaged in orifices pierced in the wall of the central segment 7 at the bottom of the circular groove 18.

Preferably, two diametrically opposite transverse studs 20 or four transverse studs 20 spaced apart at 90° are used. The transverse studs 20 also allow the blood withdrawal and reinjection orifices 12 and 13 to be perfectly orientated with respect to the blood stream.

Figure 7:
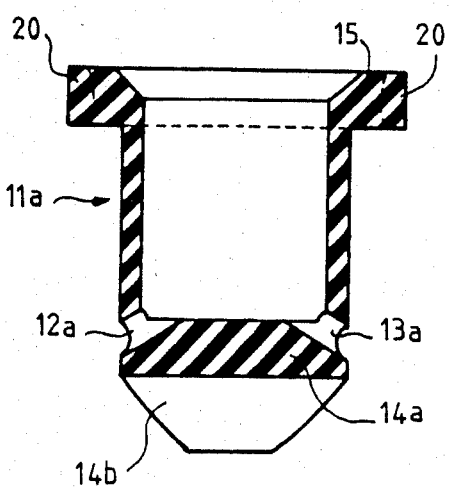
FIGS. 6 to 8 show a preferred embodiment of the tubular resilient closure element of the invention, and in particular.
Figure 6:
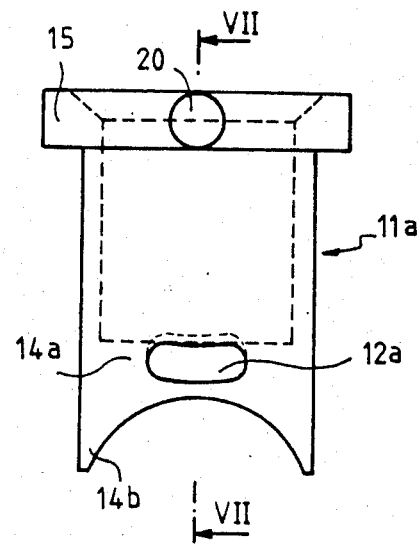
Figure 8:
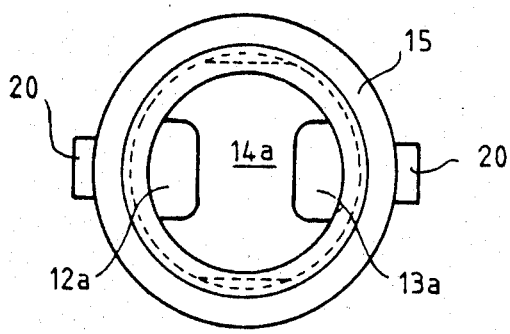

The closure element 11 of the invention may preferably have the configuration 11a illustrated in FIGS. 6 to 8.

Figure 5:
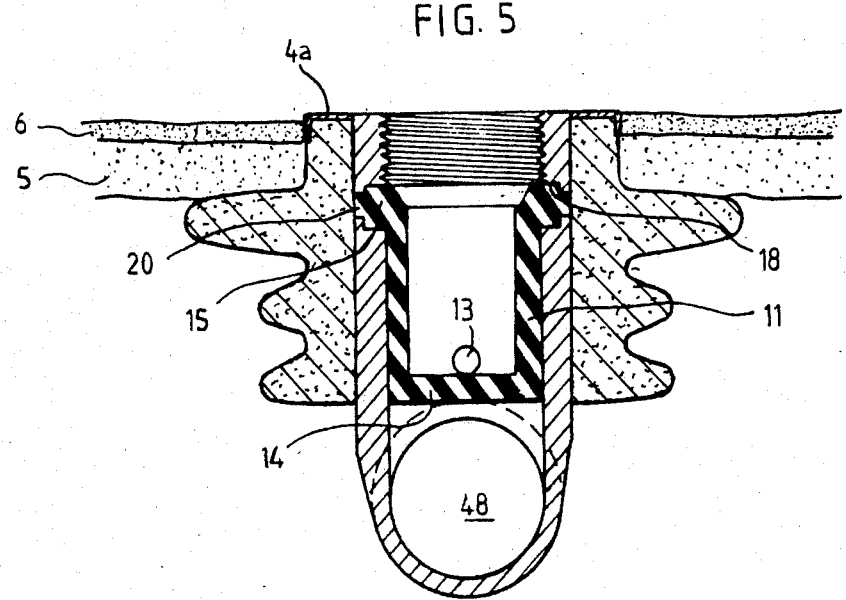
FIG. 5 corresponds to FIG. 4 in which the percutaneous device is shown with the closure element of the invention in the rest position—namely, in the absence of the blood flow control mechanism as well as the cover.

The difference between the closure element 11a and the closure element 11 shown in FIGS. 1, 4 and 5 consists essentially in that the closure element 11a comprises:

a sealing base 14a which has an arcuate configuration defined transversely (i.e., perpendicularly to the blood flow direction) by two substantially triangular lateral projections 14b which are aligned with the lateral wall of the closure element 11a. The purpose of this axial configuration, which matches the inner profile of the implantable percutaneous device 1, is to reduce the turbulence due to the immersion of the sealing base 14a of the closure element 11a in the blood stream.

lateral orifices 12a and 13a for communication with the blood stream are oblong. The blood flow axis of the orifices 12a and 13a slant (preferably by 60°) with respect to the axis of the closure element 11a and pass substantially through the point of intersection of the sealing base 14a with the side wall of the closure element 11a. The use of the oblong and slanting orifices 12a and 13a facilitates the blood flow and increases the flow rate.

Furthermore, although the closure elements 11 and 11a have been shown as being formed cylindrically, it is also possible to give the closure element a slightly tapered shape.

The blood flow control mechanism 2 is preferably made from titanium or stainless steel. The blood flow control mechanism 2 comprising two tubular flow chambers 21 and 22 separated by a central longitudinal dividing wall 23. An external sheath 24 surrounds the tubular flow chambers 21 and 22. The external sheath 24 is sized and shaped to fit snugly inside the closure element 11.

The external sheath 24 of the tubular flow chambers 21 and 22 comprises, in accordance with the invention, an annular collar 25 formed substantially in the median part of the tubular fiber chambers 21 and 22, which therefore extend bilaterally with respect to the annular collar 25. Conceptually, the annular collar 25 divides each of the tubular flow chambers 21 and 22 into a distal part and a proximal part. The annular collar 25 is sized, shaped, and positioned to cooperate with means for locking and driving the tubular flow chambers 21 and 22 inside the closure element 11. The closure element 11 is thus extended resiliently by the axial thrust of the distal part of the blood flow control mechanism 2 against the sealing base 14 of the closure element 11. Thus, the sealing base 14 of the closure element 11 is immersed in the blood stream with the withdrawal and reinjection orifices 12 and 13 in communication with the blood stream.

When the blood flow control mechanism 2 is removed, the closure element 11 resumes its initial dimensions under the action of the stress due to its resilient extension.

Communication between the withdrawal and reinjection orifices 12 and 13 and the tubular flow chambers 21 and 22, respectively, is obtained by means of two diametrically opposite transverse notches 26 and 27 which are formed at the level of the distal ends of the distal parts of the tubular flow chambers 21 and 22. Each of the transverse notches 26 and 27 has a height at least equal to the diameter of the corresponding orifices 12 and 13, respectively.

Advantageously, the transverse notches 26 and 27 have a V shape with a wide opening, preferably between 150° and 180°. This shape results in permanently providing communication with the withdrawal and reinjection orifices 12 and 13, respectively, even if the tubular flow chambers 21 and 22 are only very approximately oriented. This provides great ease of use for the operator, who has no need of tools or aligning means.

The means for locking and driving the tubular flow chambers 21 and 22 are formed by a knurled nut 28 and a fixing ring 29.

In the cylindrical body of the knurled nut 28 is formed a first central seat 30 sized, shaped, and positioned to house the annular collar 25 projecting from the external sheath 24 of the tubular flow chambers 21 and 22. A second central seat 31 is superimposed on the first central seat 30. The second central seat 31 has a larger diameter than the first central seat 30. On the side opposite the first and second central seats 30 and 31 and in communication with the latter, the knurled nut 28 has a central projecting part 32. The central projecting part 32 is threaded on its external surface and is sized, shaped, and positioned so that it can be screwed into a tapped portion 33 situated above the circular groove 18 in the central segment 7 of the percutaneous device 1.

The fixing ring 29 is coaxial with and superimposed with respect to the knurled nut 28. The fixing ring 29 is formed from two half rings 29a and 29b. Each of the half rings 29a and 29b has on its transverse face which faces the knurled nut 28 a semi-circular groove 34 surrounding centrally a part 35. The central part 35 is sized, shaped, and positioned to be received and centered in the second central seat 31 of the fixing ring 29 and to imprison, with the knurled nut 28, the annular collar 25 of the tubular flow chambers 21 and 22 in the first central seat 30.

Laterally, each semi-circular groove 34 defines a part 36 which partially envelopes the knurled nut 28.

The knurled nut 28 and the fixing ring 29 are preferably interlocked by screws 37.

It should be noted that screwing the knurled nut 28 into the central segment 7 of the percutaneous device 1 is made very easy and precise because of the distal part of the blood flow control mechanism 2 which guides and perfectly aligns the knurled nut 28 in its housing.

The cover 3 (cf. FIG. 4) closes off the percutaneous device 1 between two access operations for renal dialysis.

The cover 3 comprises a closure plate 38 for covering the central segment 7 and the distal surface of the porous coating 4.

An annular seal 39 is force fitted into a circular groove formed in the closure face of the closure plate 38. The annular seal 39 is advantageously made from elastomer.

Projecting from the closure plate 38 into the inside of the central segment 7 is a first central cylindrical part 40. The first central cylindrical part 40 is threaded on its external surface and sized, shaped, and positioned so that it can be screwed into the tapped portion 33.

A second central cylindrical part 41 extends coaxially from the first central cylindrical part 40. The second central cylindrical part 41 is smaller in diameter than the first central cylindrical part 40, and it extends inside the closure element 11. The second central cylindrical part 41 causes a pressure sleeve 42, which surrounds the second central cylindrical part 41 and which is force fitted into the closure element 11, to be aligned and centered so that the pressure sleeve 42 is compressed laterally against the wall of the central segment 7 and the pressure sleeve 42 is locked against rotation. Thus, it is possible to drive towards the blood stream defined by the lateral segments 16 and 17 any thin blood film which may possibly penetrate between the two parts 11 and 7.

A third central cylindrical part 43, projecting coaxially from the second central cylindrical part 41 and having a smaller diameter than the second central cylindrical part 41, is surrounded by a washer 44. The washer 44 has a diameter greater than that of the second central cylindrical part 41.

The washer 44 is held in position against the second central cylindrical part 41 by a splayed out portion 45 on the distal end of the third central cylindrical part 43. The splayed out portion 45 is obtained by crimping or by hot forming, depending on whether the cover 3 is made from metal or a plastic material.

A cylindrical internal groove 46 is formed in the distal part of the pressure sleeve 42. The cylindrical groove 46 extends to the sealing base 14 of the closure element 11. The washer 44 seals against a shoulder 47 at the proximal end of the cylindrical internal groove 46. Thus, the pressure sleeve 42 is imprisoned between the first central cylindrical part 40 and the washer 44.

The dimensions of the first, second, and third central cylindrical parts 40, 41, and 43 and of the pressure sleeve 42 are such that the axial pressure exerted on the sealing base 14 of the closure element 11 which, from the position of rest shown in FIG. 5, is born by the cover 3 in the position of alignment with the base 19 of the central segment 7, is tangent to the upper limit of the aperture 48 of the blood shunt defined by the lateral segments 16 and 17 of the percutaneous device 1.

When it is desired to carry out a renal dialysis operation, after removing the cover 3, the distal parts of the tubular flow chambers 21 and 22 are inserted in the closure element 11 by screwing the knurled nut 28 in the central segment 7 of the percutaneous device 1.

During screwing, the end of the distal parts of the tubular flow chambers 21 and 22 come into abutment against the sealing base 14 of the closure element 11. Thus abutment causes the resilient extension of the closure element 11 and places the withdrawal and reinjection orifices 12 and 13 in contact, and so the tubular flow chambers 21 and 22, through the transverse notches 26 and 27, with the blood contained in the lateral segments 16 and 17.

The connection between the tubular flow chambers 21 and 22 and the cleansing device (not shown) is provided by means of two end pieces 49 which are placed one behind the other and only one of which is visible in the drawings. Sealing between the end pieces 49 and the tubular flow chambers 21 and 22 is provided by seals 50.

The end pieces 49 are not parallel, but converge towards the tubular flow chambers 21 and 22.

In so far as the possible replacement of the closure element 11 of the percutaneous device 1 is concerned, this is effected in a very simple way. The annular retaining collar 15 is removed, and the transverse studs 27 are removed from their housings by resilient deformation of the closure element 11 after outwardly nipping the arterial-venous shunt situated at the right and at the left of the central segment 7 of the percutaneous device 1. The implantation of the arterial-venous shunt is well known by the patient and/or the operator. Generally, the percutaneous device 1 is implanted at the level of the biceps perpendicularly to this muscle.

This nipping is necessary to minimize the loss of blood during removal of a worn closure element and replacement thereof by a new closure element.

As is clear from the foregoing, the invention is in no wise limited to those of its embodiments and modes of application which have been described explicity. It embraces on the contrary all variants thereof which may occur to technicians skilled in the matter, without departing from the scope or spirit of the present invention. For example, although the blood flow control mechanism has been shown as being preferably provided with two flow chambers (or ducts), it is obvious that a control mechanism could also be used having a single chamber (or duct).

What is claimed is:

1. A device for a traumatic access to the blood circuit, said device comprising in combination:
    (a) an implantable device having a tubular segment for access to a blood vessel which, in use, projects slightly from the cutaneous surface;
    (b) a closure element for resiliently closing said tubular segment;
    (c) a control mechanism for controlling the blood flow through said closure element, said control mechanism having a proximal part and a distal part; and
    (d) a cover for sealing said tubular segment;
wherein:
    (e) said closure element is a tubular piece made from a resilient hemocompatible material inserted inside said tubular segment;
    (f) said closure element is closed at its base and is provided with at least one lateral orifice for communication with a blood vessel during use;

(g) said at least one lateral orifice is closed by the wall of said tubular segment when said closure element is not resiliently extended;

(h) said closure element is resiliently extended when said control mechanism is inserted in said tubular segment by the axial thrust of said distal part of said control mechanism on the base of said closure element, thereby immersing the base of said closure element and said at least one orifice in the blood stream during use of the device;

(i) said closure element resumes its initial dimensions under the action of the stress due to its resilient extension when said control mechanism is removed; and (j) the base of said closure element has an outwardly arcuate configuration for reducing turbulance due to the immersion of the base in the blood stream, which arcuate configuration is defined transversely (namely, perpendicularly to the blood flow direction) by two at least substantially triangular lateral projections which are aligned with a lateral wall of said closure element.

2. A device for a traumatic access to the blood circuit, said device comprising in combination:

(a) an implantable device having a tubular segment for access to a blood vessel which, in use, projects slightly from the cutaneous surface;

(b) a closure element for resiliently closing said tubular segment;

(c) a control mechanism for controlling the blood flow through said closure element, said control mechanism having a proximal part and a distal part; and (d) a cover for sealing said tubular segment;

wherein:

(e) said closure element is a tubular piece made from a resilient hemocompatible material inserted inside said tubular segment;

(f) said closure element is closed at its base and is provided with at least one lateral orifice for communication with a blood vessel during use;

(g) said at least one lateral orifice is closed by the wall of said tubular segment when said closure element is not resiliently extended;

(h) said closure element is resiliently extended when said control mechanism is inserted in said tubular segment by the axial thrust of said distal part of said control mechanism on the base of said closure element, thereby immersing the base of said closure element and said at least one orifice in the blood stream during use of the device;

(i) said closure element resumes its initial dimensions under the action of the stress due to its resilient extension when said control mechanism is removed;

(j) said cover comprises a closure plate sized and shaped to cover said tubular segment and a first central cylindrical part which projects from said closure plate and which is threaded and sized and shaped to be screwed into a tapped portion of said tubular segment;

(k) said cover further comprises a second central cylindrical part, said second central cylindrical part being smaller in diameter than said first central cylindrical part;

(l) said second central cylindrical part juts from said first central cylindrical part into said closure element;

(m) said second central cylindrical part is surrounded by a pressure sleeve extending as far as the base of said closure element and being force fitted therein;

(n) said pressure sleeve is secured against rotation and compresses the lateral wall of said closure element against the wall of said tubular segment of said implantable device while allowing free rotation of said second central cylindrical part inside said pressure sleeve;

(o) said cover further comprises a third central cylindrical part which projects from said second central cylindrical part, said third central cylindrical part being smaller in diameter than said second central cylindrical part;

(p) said third central cylindrical part is surrounded by a retaining washer having an outer diameter greater than the diameter of said second central cylindrical part;

(q) said retaining washer is held against said second central cylindrical part by a splayed out portion of the distal end of said third central cylindrical part;

(r) said retaining washer is housed in a cylindrical groove formed in the distal part of said pressure sleeve, in the internal wall thereof, said cylindrical groove defining in the internal wall a shoulder against which said retaining washer is seated; and (s) said retaining washer holds said pressure sleeve in position.

3. A device for atraumatic access to the blood circuit, said device comprising in combination:

(a) an implantable device having a tubular segment for access to a blood vessel which, in use, projects slightly from the cutaneous surface;

(b) a closure element for resiliently closing said tubular segment;

(c) a control mechanism for controlling the blood flow through said closure element, said control mechanism having a proximal part and a distal part; and (d) a cover for sealing said tubular segment;

wherein:

(e) said closure element is a tubular piece made from a resilient hemocompatible material inserted inside said tubular segment;

(f) said closure element is closed at its base and is provided with at least one lateral orifice for communication with a blood vessel during use;

(g) said at least one lateral orifice is closed by the wall of said tubular segment when said closure element is not resiliently extended;

(h) said closure element is resiliently extended when said control mechanism is inserted in said tubular segment by the axial thrust of said distal part of said control mechanism on the base of said closure element, thereby immersing the base of said closure element and said at least one orifice in the blood stream during use of the device;

(i) said closure element resumes its initial dimensions under the action of the stress due to its resilient extension when said control mechanism is removed;

(j) said control mechanism comprises two tubular flow chambers which, in use, communicate with two end pieces connected to a blood cleansing device;

(k) said two tubular flow chambers are provided with two diametrically opposite notches;

(l) each one of said two diametrically opposite notches is in the form of a V with a wide opening;

(m) said two tubular flow chambers are joined together by a central longitudinal dividing wall;

(n) said two tubular flow chambers are surrounded by an external sheath;

(o) said external sheath has an annular collar formed at least substantially at its median part;

(p) said two tubular flow chambers extend bilaterally into said distal and proximal parts of said control mechanism;

(q) said annular collar is sized, shaped, and positioned to cooperate with means for locking said two tubular flow chambers and for driving said distal part of said control mechanism by a roto-translation into said closure elements;

(r) said means for locking and driving comprises a knurled nut the cylindrical body of which comprises a first central seat housing said annular collar, a second central seat superimposed on said first central seat and of larger diameter than said first central seat, and a central projecting part disposed on the side opposite said first and second central seats, said central projecting part being in communication with said first and central seats and being threaded on its external surface for screwing into a tapped portion of said tubular segment;

(s) said means for locking and driving further comprises a fixing ring coaxial and superimposed with respect to said knurled nut;

(t) said fixing ring is formed of two half rings each comprising, on a transverse base, a semicircular groove defining centrally a part sized, shaped, and positioned to be housed and centered in said second central seat and to imprison, with said knurled nut, said annular collar in said first central seat;

(u) said semicircular grooves defines laterally a part sized, shaped, and positioned to partially envelope said knurled nut; and (v) said two half rings and said knurled nut are releasably secured together.

4. The device as claimed in claim 3 wherein the porosity of said porous coating is between 40% and 50% of the initial porosity of said carbon fiber porous substrate.

5. A device for atraumatic access to a blood vessel of a living organism through the cutaneous surface thereof, said device comprising in combination:

(a) an implantable device comprising a rigid tubular segment having a distal end for access to a blood vessel and a proximal end which, in use, projects slightly from the cutaneous surface;

(b) a valving element for said rigid tubular segment;

(c) a control mechanism for controlling the blood flow through said valving element, said control mechanism comprising at least one tubular flow chamber having a proximal part and a distal part which, in use, communicates with an end piece which is connected to a blood cleansing device;

(d) a porous coating adapted to be colonized by tissue ingrowth, said porous coating at least partially surrounding said implantable device; and (e) a cover for sealing the proximal end of said rigid tubular segment in the absence of said control mechanism, (f) said porous coating be formed from a carbon-carbon composite material comprising a reinforcement formed from a carbon fiber porous substrate embedded in a carbonaceous matrix which only partially densifies said carbon fiber porous substrate while connecting the carbon fibers together, the porosity of said carbon-carbon composite material being equal to or less than 50% of the initial porosity of said carbon fiber porous substrate.

6. The device as claimed in claim 5 wherein said porous coating has a configuration comprising:

(a) a substantially cylindrical proximal part surrounding the portion of said rigid tubular segment of said implantable device which, in use, projects slightly from the epiderm, the height of said proximal part of said porous coating being slightly greater than the total thickness of the derm and of the epiderm of the living organism;

(b) a circular collar-shaped intermediate part following said proximal part of said porous coating, said intermediate part providing the main biological anchorage and, in use, being disposed just under the derm; and (c) a distal part comprising a plurality of circular ribs providing an additional biological anchorage, (d) said porous coating surrounding said rigid tubular segment completely over the whole of its length.

7. The device as claimed in claim 6 and further comprising a solid pyrolytic carbon film which is sealing and non-porous formed on said proximal part of said porous coating, said film being applied to the exposed portions of said porous coating parallel to the epiderm and to a small portion of its external lateral surface perpendicular to the epiderm.

8. A device for atraumatic access to a blood vessel of a living organism through the cutaneous surface thereof, said device comprising in combination:

(a) an implantable device comprising a rigid tubular segment having a distal end for access to a blood vessel and a proximal end which, in use, projects slightly from the cutaneous surface;

(b) a resilient tubular valving element having a proximal end and a distal end, said resilient tubular valving element being closed at its distal end and being provided with at least one lateral orifice in its lateral wall for communication with a blood vessel, said resilient tubular valving element being sized and shaped so that it can be inserted inside said rigid tubular segment;

(c) a control mechanism for controlling the blood flow through said valving element, said control mechanism comprising at least one tubular flow chamber having a proximal part and a distal part which, in use, communicates with an end piece which is connected to a blood cleansing device;

(d) a porous coating adapted to be colonized by tissue ingrowth, said porous coating at least partially surrounding said implantable device; and (e) a cover for sealing the proximal end of said rigid tubular segment in the absence of said control mechanism;

(f) said at least one tubular flow chamber being provided at its distal end with a notch and comprising substantially in its median part an annular collar with respect to which said at least one tubular flow chamber extends bilaterally into said distal and proximal parts;

(g) said annular collar being sized, shaped, and positioned to cooperate with means for locking said at least one tubular flow chamber and for driving said distal part of said at least one tubular flow chamber by roto-translation into said resilient tubular valving element;

(h) said at least one lateral orifice in said resilient tubular valving element being closed by the wall of said rigid tubular segment in the absence of said control mechanism;

(i) said resilient tubular valving element being resiliently extended and said at least one lateral orifice communicating with said notch when said control mechanism is present;

(j) the extension of said resilient tubular valving element being obtained by the axial thrust of said distal part of said control mechanism on the closed end of said resilient tubular valving element, thereby immersing the distal end of said resilient tubular valving element and said at least one lateral orifice in the blood stream;

(k) said resilient tubular valving element resuming its initial dimensions under the action of the stress due to its resilient extension when said control mechanism is removed; and (l) said porous coating being formed from a carbon-carbon composite material comprising a reinforcement formed from a carbon porous substrate embedded in a carbonaceous matrix which only partially densifies said carbon fiber porous substrate while connecting the carbon fibers together, the porosity of said carbon-carbon composite material being equal to or less than 50% of the initial porosity of said carbon fiber porous substrate.

9. The device as claimed in claim 8 wherein the porosity of said porous coating is between 40% and 50% of the initial porosity of said carbon fiber porous substrate.

10. The device as claimed in claim 8 wherein said porous coating has a configuration comprising:
(a) a substantially cylindrical proximal part surrounding the portion of said rigid tubular segment of said implantable device which, in use, projects slightly from the epiderm, the height of said proximal part of said porous coating being slightly greater than the total thickness of the derm and of the epiderm of the living organism;
(b) a circular collar-shaped intermediate part following said proximal part of said porous coating, said intermediate part providing the main biological anchorage and, in use, being disposed just under the derm; and
(c) a distal part comprising a plurality of circular ribs providing an additional biological anchorage,
(d) said porous coating surrounding said rigid tubular segment completely over the whole of its length.

11. The device as claimed in claim 8 and further comprising a solid pyrolytic carbon film which is sealing and non-porous formed on said proximal part of said porous coating, said film being applied to the exposed portions of said porous coating parallel to the epiderm and to a small portion of its external lateral surface perpendicular to the epiderm.

12. The device as claimed in claim 8 wherein said means for locking and driving said at least one tubular flow chamber comprise:
(a) a knurled nut the cylindrical body of which comprises:
  (i) a first central seat housing said annular collar projecting from said at least one tubular flow chamber;
  (ii) a second central seat superimposed on said first central seat and of larger diameter than said first central seat; and
  (iii) a central projecting part disposed on the side opposite said first and second central seats, said central projecting part being in communication with said first and second central seats and being threaded on its external surface for screwing into the proximal end of said rigid tubular segment, and
(b) a fixing ring that is coaxial and superposed with respect to said knurled nut, said fixing ring comprises two half rings, each one of said two half rings comprising, on a transverse base, a semicircular groove defining centrally a part sized, shaped, and positioned to be housed and centered in said second central seat and to imprison, with said knurled nut, said annular collar of said at least one tubular flow chamber in said first central seat, said semicircular grooves defining laterally a part sized, shaped, and positioned to partially envelope said knurled nut, said two half rings and said knurled nut being releasably secured together.

13. The device as claimed in claim 8 wherein said cover comprises in combination:
(a) a closure plate sized and shaped to cover said rigid tubular segment;
(b) a first central cylindrical part which projects from said closure plate, which is threaded, and which is sized, shaped, and positioned so that it can be screwed into the proximal end of said rigid tubular segment in the absence of said control mechanism;
(c) a second central cylindrical part, smaller in diameter than said first central cylindrical part, said second central cylindrical part jutting from said first central cylindrical part inside said resilient tubular valving element, said second central cylindrical part being surrounded by a pressure sleeve force fitted inside said resilient tubular valving element and sized and shaped to press said resilient tubular valving element radially against said rigid tubular segment, said pressure sleeve being therefore secured against rotation while allowing free rotation of said second central cylindrical part inside said pressure sleeve; and
(d) a third central cylindrical part which projects from said second central cylindrical part and which has a smaller diameter than said second cylindrical part, said third cylindrical part being surrounded by a retaining washer, said retaining washer having an external diameter greater than the diameter of said second central cylindrical part, said retaining washer being held against said second cylindrical part by a splayed out portion of the distal end of said third central cylindrical part, said retaining washer being housed in an internal cylindrical groove formed in the distal part of said pressure sleeve, said internal cylindrical groove defining a shoulder against which said retaining washer is held, said retaining washer holding said pressure sleeve in position.

14. The device as claimed in claim 8 wherein the distal end of said resilient tubular valving element has an arcuate outward configuration for reducing the turbulance due to the immersion of the distal end of said resilient tubular valving element in the blood stream, which arcuate configuration is defined transversely (namely, perpendicularly to the blood flow direction)

by two at least substantially triangular lateral projections which are aligned with the lateral wall of said resilient tubular valving element.

15. The device as claimed in claim 8 and further comprising means retaining said resilient tubular valving element in said rigid tubular segment, said means comprising an annular collar formed about the proximal end of said resilient tubular valving element, said annular collar being provided with a plurality of transverse anti-rotation studs formed on said annular collar, said rigid tubular segment having a circular groove in which is housed said annular collar of said resilient tubular valving element, said transverse anti-rotation studs being housed in orifices pierced in the wall of said rigid tubular segment, and said circular groove being formed in the internal wall of said rigid tubular segment at a distance from the proximal end of said rigid tubular segment such that, in the absence of application of said control mechanism or of said cover, the distal end of said resilient tubular valving element is set back with respect to the distal end of said rigid tubular segment.

16. The device as claimed in claim 8 wherein said at least one lateral orifice is oblong and is formed with the blood flow access of said at least one lateral orifice slanting with respect to the access of said resilient tubular valving element and passing substantially through the point of intersection between the closed end and the lateral wall of said resilient tubular valving element.

17. The device as claimed in claim 16 wherein said blood flow access is slanted by at least approximately 60° with respect to the access of said resilient tubular valving element.

* * * * *